(12) United States Patent
Matusz et al.

(10) Patent No.: US 7,259,129 B2
(45) Date of Patent: Aug. 21, 2007

(54) SILVER-CONTAINING CATALYSTS, THE MANUFACTURE OF SUCH SILVER-CONTAINING CATALYSTS, AND THE USE THEREOF

(75) Inventors: Marek Matusz, Houston, TX (US); Michael Alan Richard, Fulshear, TX (US); John Robert Lockemeyer, Sugar Land, TX (US); Alouisius Nicolaas Renee Bos, Amsterdam (NL); Dominicus Maria Rekers, The Hague (NL); Donald Reinalda, Amsterdam (NL); Randall Clayton Yeates, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/816,543

(22) Filed: Apr. 1, 2004

(65) Prior Publication Data

US 2004/0260103 A1    Dec. 23, 2004

Related U.S. Application Data

(63) Continuation-in-part of application No. 10/431,189, filed on May 7, 2003, now abandoned.

(51) Int. Cl.
    *B01J 23/50*    (2006.01)
(52) U.S. Cl. ..................... 502/347; 502/348
(58) Field of Classification Search ............. 502/347, 502/348
    See application file for complete search history.

(56) References Cited

U.S. PATENT DOCUMENTS

| | | | |
|---|---|---|---|
| 2,424,083 A | 7/1947 | Finch et al. | |
| 2,901,441 A | 8/1959 | Waterman | |
| 3,563,913 A | 2/1971 | De Krijger | 252/463 |
| 3,563,914 A | 2/1971 | Wattiemena | 252/463 |
| 3,844,981 A | 10/1974 | Cusumano | 252/471 |
| 3,895,093 A | 7/1975 | Weidenbach et al. | 423/213.5 |
| 3,937,476 A | 2/1976 | Sakai | 274/39 A |
| 3,962,136 A | 6/1976 | Nielsen et al. | 252/454 |
| 3,962,285 A | 6/1976 | Cusumano | 260/348 |
| 3,972,829 A | 8/1976 | Michalko | |
| 3,997,476 A | 12/1976 | Cull | |
| 4,005,049 A | 1/1977 | Fields | |
| 4,033,903 A * | 7/1977 | Maxwell | 502/347 |
| 4,125,480 A | 11/1978 | Maxwell | |
| 4,186,106 A | 1/1980 | Rebsdat et al. | |
| 4,207,210 A | 6/1980 | Kilty | 252/463 |
| 4,212,772 A | 7/1980 | Mross et al. | 252/476 |
| 4,235,798 A | 11/1980 | Bartley et al. | |
| 4,244,889 A | 1/1981 | Bartley et al. | 564/132 |
| 4,356,312 A | 10/1982 | Nieslen et al. | 549/534 |
| 4,361,500 A | 11/1982 | Mathe et al. | 252/430 |
| 4,361,503 A | 11/1982 | Dwyer et al. | |
| 4,361,504 A | 11/1982 | Solomon et al. | |
| 4,366,092 A | 12/1982 | Winterton | |
| 4,366,093 A | 12/1982 | Shiozaki et al. | |
| 4,367,167 A | 1/1983 | Lee et al. | |
| 4,368,144 A | 1/1983 | Mitsuhata et al. | |
| 4,379,134 A | 4/1983 | Weber et al. | 423/626 |
| 4,382,149 A | 5/1983 | Krueger | 568/473 |
| 4,420,420 A | 12/1983 | Mita et al. | 502/261 |
| 4,458,032 A | 7/1984 | Rebsdat et al. | 502/348 |
| 4,471,071 A | 9/1984 | Rebsda et al. | 502/347 |
| 4,511,671 A | 4/1985 | Saito et al. | 502/242 |
| 4,532,231 A * | 7/1985 | Johnson | 502/347 |
| 4,628,129 A | 12/1986 | Bartley | 568/864 |
| 4,645,754 A | 2/1987 | Tamura et al. | 502/527 |
| 4,656,157 A | 4/1987 | Hofmann et al. | 502/439 |
| 4,665,048 A | 5/1987 | Van Leeuwen et al. | 502/221 |
| 4,728,634 A | 3/1988 | Boxhoorn et al. | 502/243 |
| 4,731,350 A | 3/1988 | Boxhoorn et al. | 502/231 |
| 4,761,394 A | 8/1988 | Lauritzen | 502/348 |
| 4,766,105 A | 8/1988 | Lauritzen | 502/216 |
| 4,797,270 A | 1/1989 | Alvarado Cendan et al. | 423/625 |
| 4,797,279 A | 1/1989 | Karamata et al. | 424/93 |
| 4,808,738 A | 2/1989 | Lauritzen | 549/536 |
| 4,810,689 A | 3/1989 | Hayden | 502/347 |
| 4,820,675 A | 4/1989 | Lauritzen | 502/216 |
| 4,829,044 A | 5/1989 | Boxhorn et al. | 502/348 |
| 4,837,194 A | 6/1989 | Hayden | 502/348 |
| 4,845,296 A | 7/1989 | Ahmed et al. | 564/477 |

(Continued)

FOREIGN PATENT DOCUMENTS

DE    1920976    11/1969

(Continued)

OTHER PUBLICATIONS

Brunauer, Emmett, Teller, J. Am. Chem. Soc. 60 (1938) pp. 309-319.

(Continued)

*Primary Examiner*—Elizabeth D. Wood

(57) ABSTRACT

A high activity and high selectivity silver catalyst comprising silver and, optionally, one or more promoters supported on a suitable support material having the form of a shaped agglomerate. The structure of the shaped agglomerate is that of a hollow cylinder having a relatively small inside (bore) diameter. The catalyst is made by providing the shaped material of a particular geometry and incorporating the catalytic components therein. The catalyst is useful in the epoxidation of ethylene.

15 Claims, 2 Drawing Sheets

U.S. PATENT DOCUMENTS

| | | | | |
|---|---|---|---|---|
| 4,874,739 | A | 10/1989 | Boxhoorn | 502/218 |
| 4,886,917 | A | 12/1989 | Knopf et al. | 568/623 |
| 4,908,343 | A | 3/1990 | Bhasin | 502/218 |
| 4,916,243 | A | 4/1990 | Bhasin et al. | 549/534 |
| 4,939,114 | A | 7/1990 | Nojiri et al. | 502/348 |
| 4,994,587 | A | 2/1991 | Notermann et al. | 549/534 |
| 4,994,588 | A | 2/1991 | Kapicak et al. | 549/534 |
| 4,994,589 | A | 2/1991 | Notermann | 549/534 |
| 5,037,794 | A | 8/1991 | Magistro | 502/355 |
| 5,055,442 | A | 10/1991 | Osaka et al. | 502/439 |
| 5,057,481 | A | 10/1991 | Bhasin | 502/208 |
| 5,100,859 | A * | 3/1992 | Gerdes et al. | 502/439 |
| 5,112,795 | A | 5/1992 | Minahan et al. | 502/324 |
| 5,145,824 | A | 9/1992 | Buffum et al. | 502/216 |
| 5,187,140 | A | 2/1993 | Thorsteinson | 502/348 |
| 5,254,786 | A | 10/1993 | Lin et al. | 585/645 |
| 5,364,826 | A | 11/1994 | Kemp | 502/315 |
| 5,374,748 | A | 12/1994 | Rizkalla | 549/534 |
| 5,380,697 | A | 1/1995 | Matusz et al. | 502/348 |
| 5,380,885 | A | 1/1995 | Kemp | 549/536 |
| 5,387,751 | A | 2/1995 | Hayden et al. | 549/534 |
| 5,407,888 | A | 4/1995 | Herzog et al. | 502/317 |
| 5,418,202 | A | 5/1995 | Evans et al. | 502/348 |
| 5,447,897 | A | 9/1995 | Kemp | 502/303 |
| 5,457,897 | A | 10/1995 | Becker | 34/472 |
| 5,486,628 | A | 1/1996 | Kemp | 549/536 |
| 5,502,020 | A | 3/1996 | Iwakura et al. | 502/347 |
| 5,545,603 | A | 8/1996 | Kemp | 502/347 |
| 5,588,986 | A | 12/1996 | Davis et al. | 95/211 |
| 5,597,773 | A | 1/1997 | Evans et al. | 502/348 |
| 5,626,455 | A | 5/1997 | Keller et al. | 414/288 |
| 5,663,385 | A | 9/1997 | Kemp | 549/536 |
| 5,668,077 | A | 9/1997 | Klopries et al. | 502/347 |
| 5,703,253 | A | 12/1997 | Evans et al. | 549/536 |
| 5,705,661 | A | 1/1998 | Iwakura et al. | 549/536 |
| 5,734,068 | A | 3/1998 | Klopries et al. | 549/536 |
| 5,739,075 | A | 4/1998 | Matusz | 502/302 |
| 5,801,259 | A | 9/1998 | Kowaleski | 549/536 |
| 5,935,894 | A | 8/1999 | Kanazirev | 502/341 |
| 6,103,916 | A | 8/2000 | Takada et al. | 549/534 |
| 6,281,160 | B1 | 8/2001 | Basset et al. | 502/332 |
| 6,325,919 | B1 | 12/2001 | Koyama et al. | 208/134 |
| 6,368,998 | B1 | 4/2002 | Lockemeyer | 502/347 |
| 6,498,122 | B2 | 12/2002 | Nakashiro | 502/347 |
| 6,511,938 | B1 | 1/2003 | Liu et al. | 503/347 |
| 6,631,890 | B1 | 10/2003 | Lau | 261/94 |
| 6,656,874 | B2 | 12/2003 | Lockemeyer | 502/347 |
| 2002/0010094 | A1 | 1/2002 | Lockemeyer | 502/439 |
| 2002/0010378 | A1 | 1/2002 | Kakimoto et al. | 568/867 |
| 2004/0224841 | A1* | 11/2004 | Matusz et al. | 502/347 |
| 2004/0225138 | A1 | 11/2004 | McAllister et al. | 549/523 |

FOREIGN PATENT DOCUMENTS

| | | |
|---|---|---|
| EP | 211521 A1 | 2/1987 |
| EP | 266015 A1 | 5/1988 |
| EP | 0327356 A1 | 8/1989 |
| EP | 563 414 A1 | 10/1993 |
| EP | 568978 A1 | 11/1993 |
| EP | 716884 A2 | 6/1996 |
| EP | 0937498 A1 | 8/1999 |
| EP | 1201301 A1 | 5/2002 |
| EP | 1277698 A2 | 1/2003 |
| FR | 2005978 | 10/1969 |
| GB | 1257352 | 12/1971 |
| GB | 1489335 | 10/1977 |
| JP | 56105750 | 8/1981 |
| JP | 56164013 | 12/1981 |
| WO | 96/23585 | 8/1996 |
| WO | 96/41848 | 12/1996 |
| WO | 02/26370 A1 | 9/2001 |
| WO | 2004/101144 | 11/2004 |

OTHER PUBLICATIONS

Kirk-Othmer Ency. Of Chem. Technology, 3$^{rd}$ Ed., vol. 9, 1980, pp. 432-471.

International Search Report of PCT/US2004/14088 dated Aug. 11, 2004.

Written Opinion of PCT/US2004/14088, Aug. 11, 2004.

International Preliminary Report on Patentability of PCT/US2004/14088, Aug. 11, 2005.

International Search Report of PCT/US2004/14087 dated Sep. 23, 2004.

Written Opinion of PCT/US2004/14087, Sep. 23, 2004.

International Preliminary Report on Patentability of PCT/US2004/14087, OCT. 28, 2005.

Fulton, J. W., "Selecting the Catalyst Configuration", Chemical Engineering, May 12, 1986, p. 97-101.

International Search Report of PCT/US2005/010996 dated Jul. 29, 2005.

Written Opinion of PCT/US2005/010996, Jul. 29, 2005.

International Search Report of PCT/US2005/033758 dated Jun. 12, 2006.

Written Opinion of PCT/US2005/033758, Jun. 12, 2006.

W.J. Beek, K.M.K. Muttzall: Transport Phenomena , 1975, J. Wiley & Sons, XP009060252. pp. 98-120, no month.

* cited by examiner

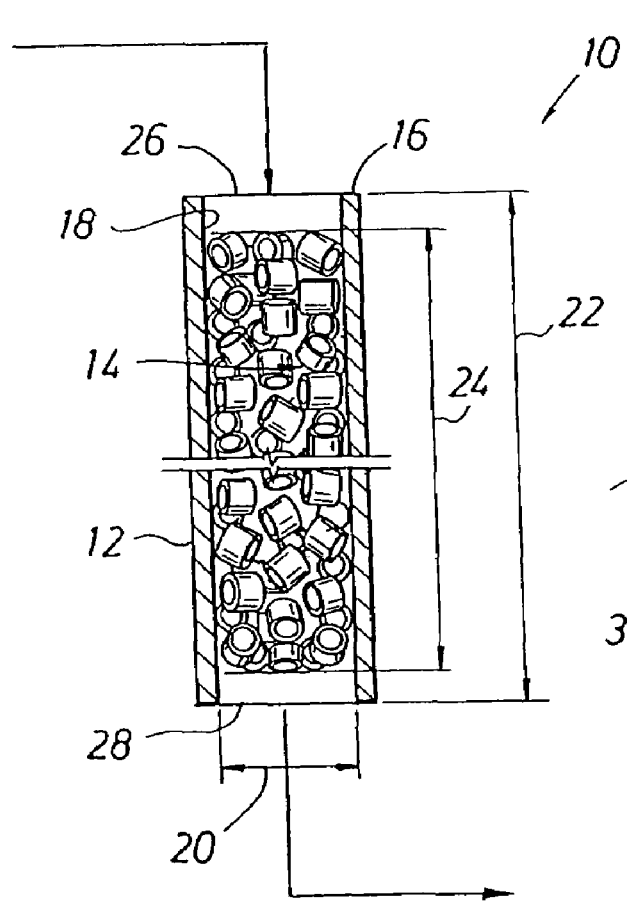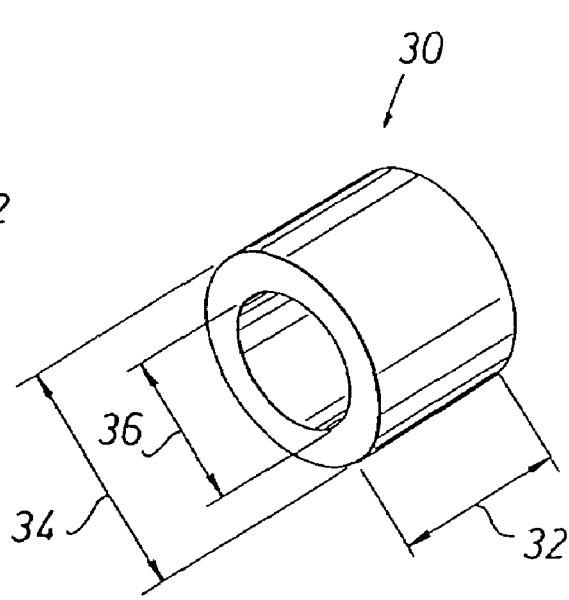

Fig. 3
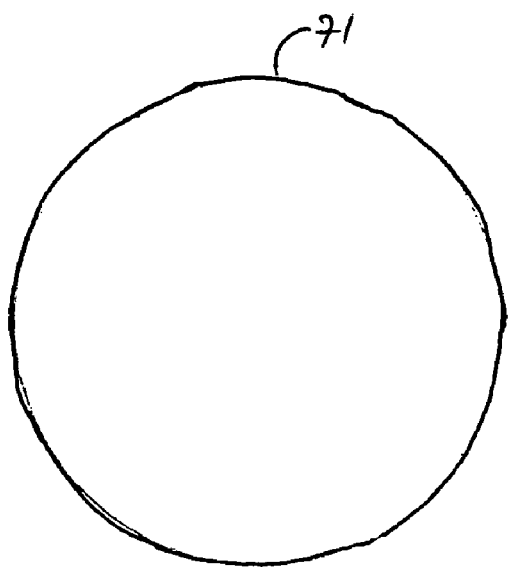
(a)
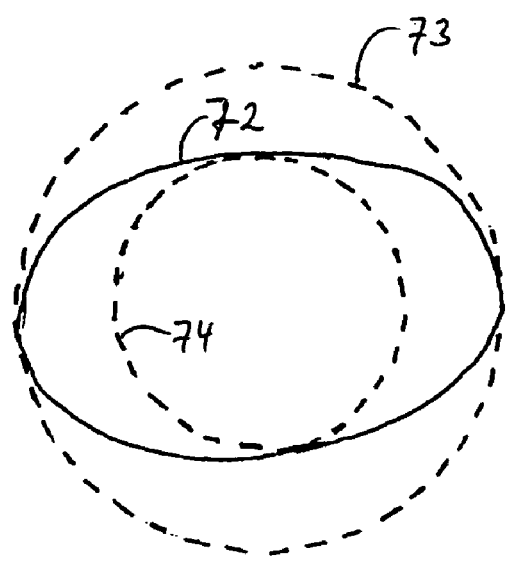
(b)

SILVER-CONTAINING CATALYSTS, THE MANUFACTURE OF SUCH SILVER-CONTAINING CATALYSTS, AND THE USE THEREOF

This application is a continuation-in-part of U.S. patent application Ser. No. 10/431,189 filed May 7, 2003, now abandoned the entire disclosure of which is hereby incorporated by reference.

This invention relates to silver-containing catalyst compositions that are particularly suitable for use in the manufacture of ethylene oxide.

Ethylene oxide is an important industrial chemical used as a feedstock for making such chemicals as ethylene glycol, ethylene glycol ethers, alkanol amines and detergents. One method of manufacturing ethylene oxide is by the catalyzed partial oxidation of ethylene with oxygen. There are continuing efforts to develop catalysts that can improve the operating efficiency of such ethylene oxide manufacturing processes. Some of the desirable properties of an ethylene oxide catalyst include good selectivity, good activity, and long catalyst life.

It is, thus, an object of this invention to provide a catalyst that has certain desirable catalytic properties that make it particularly suitable for use in the manufacture of ethylene oxide.

It is another object of this invention to provide a method of making a catalyst that exhibits at least some of the aforementioned desirable catalytic properties.

Yet another object of this invention is to provide an economically efficient process for manufacturing ethylene oxide by utilizing a catalyst having certain desirable catalytic properties.

Other aspects, objects and the several advantages of the invention will become more apparent in light of the following disclosure.

According to one aspect of the invention, a catalyst is provided which comprises silver deposited on a shaped support material having a hollow cylinder geometric configuration such that the length-to-outside diameter ratio of said shaped support material is in the range of from about 0.3 to about 2 and the internal diameter is in the range upwardly to about 30 percent of the outside diameter of said shaped support material. Suitably, the catalyst has a high silver concentration and at least one promoter compound, and the silver and promoter compound are preferably supported on a support material having a high water pore volume.

According to another aspect of the invention, a method is provided for making the catalyst of this invention. Suitably, the method involves providing a shaped support material and impregnating the shaped support material with a silver-containing solution such that the amount of silver metal in the shaped support material exceeds 15 weight percent of the weight of the shaped support material, in particular exceeds 15 weight percent of the weight of the catalyst. The silver impregnated shaped support material is then heat treated to provide the catalyst, for example in a temperature range of from 100 to 500° C., preferably from 150 to 300° C.

According to yet another aspect of the invention, a packed catalyst bed is provided which is formed from catalyst particles comprising silver supported on a shaped support, which catalyst bed has a silver loading of at least 150 kg silver/$m^3$ catalyst bed.

According to yet another aspect of the invention, the above described catalyst, a catalyst made by the above-described method, or the above described catalyst bed is used in a process for manufacturing ethylene oxide by contacting the catalyst, under suitable epoxidation process conditions, with a feed stream that comprises ethylene and oxygen.

Further, the invention provides a method of using ethylene oxide for making ethylene glycol, an ethylene glycol ether or an 1,2-alkanolamine comprising converting ethylene oxide into ethylene glycol, the ethylene glycol ether, or the 1,2-alkanolamine, wherein the ethylene oxide has been obtained by the process for preparing ethylene oxide according to this invention.

FIG. 1 depicts certain aspects of a reactor tube that includes a packed catalyst bed comprising the catalyst of this invention;

FIG. 2 depicts the shaped support for use in the invention and which has a hollow cylinder geometric configuration and the physical dimensions that characterize the shaped support material; and FIG. 3 depicts drawings of the cross-sections of the outside perimeters of (a) the shaped support material being an ideal cylinder, and (b) a cross-section of the shaped support material being a deviation from an ideal cylinder.

The catalyst composition of the present invention is a novel combination of catalytic components and support material. The support material has specific physical properties and is preferably formed into a shaped agglomerate of the support material having a hollow cylinder geometric configuration or structure with a relatively small internal diameter. "Relatively small" is herein to be understood as meaning smaller than conventionally applied in such catalysts. Also, as used herein, the terms "carrier" and "support" have the same meaning and have been used herein interchangeably.

An important aspect of this invention is the recognition that a substantial improvement can be obtained in catalyst performance, which includes the initial performance in activity and selectivity and also the activity stability and selectivity stability, for example, by changing the ratio of the nominal outside diameter to the nominal inside diameter of the hollow cylinder geometric configuration. This is truly unexpected because catalysts based on hollow cylinder support materials have been employed in processes for the manufacture of ethylene oxide already for many years and much effort has been devoted to improving the performance of such catalyst. However, attempts to improve the performance of these catalysts by modifying the geometry; of the hollow cylinder geometric configuration do not seem to have received attention.

The support material of the catalyst composition can be any porous refractory material that is relatively inert in the presence of ethylene oxidation feeds, products and reaction conditions; provided, such support material has the physical properties desired for the inventive catalyst composition especially when used to support the catalytic components of the inventive composition. Generally, the support material comprises an inorganic material, in particular an oxide, which can include, for example, alumina, silicon carbide, carbon, silica, zirconia, magnesia, silica-alumina, silica-magnesia, silica-titania, alumina-titania, alumina-magnesia, alumina-zirconia, thoria, silica-titania-zirconia and various clays.

The preferred support material comprises alumina preferably of a high purity of at least 90 weight percent alumina and, more preferably, at least 98 weight percent alumina. Frequently, the support material comprises at most 99.9 weight percent, more frequently at most 99.5 weight percent alumina. Among the various available forms of alumina alpha-alumina is the most preferred.

A particular aspect of the inventive catalyst composition is for the support material to have typically a high water absorption value generally exceeding about 40%. This high water absorption value allows for the loading of a greater amount of silver onto the support material than can be loaded onto other inorganic materials that have a lower value for water absorption. It has, thus, been found that for the inventive catalyst composition it is preferred for the water absorption of the support material to be greater than 42.5%, more preferably, greater than 45% and, most preferably, greater than 46%. Frequently, the water absorption is at most 80%, more frequently at most 70%.

As used herein, the term "water absorption" means the value as determined by test procedure ASTM C20, which is incorporated herein by reference. Water absorption is, expressed as a percentage, the weight of the water that can be absorbed into the pores of the carrier, relative to the weight of the carrier.

Typically, the support material has a mean pore diameter of 0.3 to 15 μm, preferably 1 to 10 μm; and typically a percentage of pores having a diameter of 0.03 to 10 μm of at least 50% by weight, as determined by mercury intrusion to a pressure of $3.0 \times 10^8$ Pa using a Micromeretics Autopore 9200 model (130° contact angle, mercury with a surface tension of 0.473 N/m, and correction for mercury compression applied).

The surface area of the support material as measured by the B.E.T. method can be in the range of from 0.03 $m^2/g$ to 10 $m^2/g$, preferably from 0.05 $m^2/g$ to 5 $m^2/g$ and most preferably from 0.1 $m^2/g$ to 3 $m^2/g$. Suitably, the surface area is at least 0.5 $m^2/g$. The B.E.T. method of measuring surface area has been described in detail by Brunauer, Emmet and Teller in *J. Am. Chem. Soc.* 60 (1938) 309-316, which is incorporated herein by reference.

An aspect of the inventive catalyst composition is for the support material to be in the form of a shaped agglomerate, and for the shaped agglomerate of support material to have a hollow cylinder geometric configuration with an inner diameter ("bore diameter", hereinafter), that is relatively small.

Reference is now made to FIG. 1 which depicts a reactor system 10 comprising an elongated reactor tube 12 and a packed catalyst bed 14 contained within elongated tube 12. Elongated tube 12 has a tube wall 16 with an inside tube surface 18 and inside tube diameter 20 that define a reaction zone, wherein is contained packed catalyst bed 14, and a reaction zone diameter 20. Elongated tube 12 has a tube length 22 and the packed catalyst bed 14 contained within the reaction zone has a bed depth 24. Outside the bed depth 24, the elongated tube 12 may contain a separate bed of particles of a non-catalytic material for the purpose of, for example, heat exchange with a feedstock and/or another such separate bed for the purpose of, for example, heat exchange with a reaction product. The elongated tube 12 further has an inlet tube end 26 into which the feed stream comprising ethylene and oxygen can be introduced and an outlet tube end 28 from which a reaction product comprising ethylene oxide and ethylene can be withdrawn.

The packed catalyst bed 14 contained within the reaction zone is composed of a bed of supported catalyst 30 as depicted in FIG. 2. The supported catalyst 30 is based on the support material having a generally hollow cylinder geometric configuration with a length 32, outside diameter 34, and inside or bore diameter 36.

The skilled person will appreciate that the expression "cylinder" does not necessarily mean that the hollow cylinder geometric configuration comprises an exact cylinder. The expression "cylinder" is meant to include insignificant deviations from an exact cylinder. For example, the cross-section of the outer perimeter of the hollow cylinder geometric configuration perpendicular to the cylinder axis is not necessarily an exact circle 71, as depicted in FIG. 3. Also, the axis of the hollow cylinder geometric configuration may be approximately straight and/or the outside diameter of the hollow cylinder geometric configuration may be approximately constant along the axis. Thus, insignificant deviations include, for example, cases where the outside perimeter of the cylinder can be positioned in an imaginary tube-shaped space defined by two imaginary exact coaxial cylinders of virtually the same diameters, whereby the diameter of the imaginary inner cylinder is at least 70%, more typically at least 80%, in particular at least 90%, of the diameter of the imaginary outer cylinder, and the imaginary cylinders are chosen such that the ratio of their diameters is the closest possible to 1. In such cases the diameter of the imaginary outer cylinder is deemed to be the outer diameter of the hollow cylinder geometric configuration. FIG. 3 depicts in a cross-sectional view, taken perpendicular to the axis of the imaginary cylinders 73 and 74, the outside perimeter 72 of the hollow cylinder geometric configuration, the imaginary outer cylinder 73 and the imaginary inner cylinder 74.

Similarly, the skilled person will appreciate that the bore of the hollow cylinder geometric configuration may not be necessarily exactly cylindrical, the axis of the bore may be approximately straight, the bore diameter may be approximately constant, and/or the axis of the bore may be displaced, or may angle, relative to the axis of the cylinder. If the bore diameter changes over the length of the bore, the bore diameter is deemed to be the largest diameter at a bore end. Also, the void space provided by the bore may be divided over more than one bore, for example 2, 3, or even 4, or 5 bores, in which case the diameters of the bores are such that the total of the cross-sectional areas of the bores is equal to the cross-sectional area of a single bore having a diameter, as specified herein.

In preferred embodiments, the hollow cylinder geometric configuration is intended to be a cylinder having a bore at the axis of the cylinder.

The smaller, than conventional, bore diameter helps provide for an improvement in the average crush strength of the agglomerate by offsetting the loss in crush strength that results from using a support material having a greater porosity (i.e. water absorption). Another benefit from the smaller bore diameter is that it provides for packing a greater amount of support material into the same volume, i.e., packing density, thus, allowing for more silver to be loaded into the same volume.

While it is an important aspect of the invention for the bore diameter of the shaped agglomerate to be relatively small, it is also important for the inside bore of the shaped agglomerate to have at least some dimension. It is preferred to have at least one end of the bore, preferably at both ends, a bore diameter of at least about 0.1 mm, more preferably at least about 0.2 mm. Preferably the bore diameter is at least about 0.5 mm, and preferably up to about 2 mm, for example about 1 mm or about 1.5 mm.

It has been found that the void space defined by the bore diameter provides for certain benefits in the manufacturing of the inventive catalyst and its catalytic properties. While not wanting to be bound to any particular theory, it is believed, however, that the void space provided by the bore diameter of the hollow cylinder allows for improved carrier impregnation and catalyst drying. The catalytic benefits associated with the inventive catalyst is demonstrated and discussed in more detail elsewhere herein.

The hollow cylinder geometric configuration can be defined by an outside diameter, a bore diameter, and a length. It is understood that these dimensions are nominal and approximate, since, methods of manufacturing the shaped agglomerates are not necessarily precise. The hollow cylinder may typically have a length-to-outside diameter ratio in the range of from about 0.3 to about 2, preferably from about 0.5 to about 1.6 and, most preferably, from about 0.9 to about 1.1. An important, if not critical feature of the invention is for the bore diameter to be relatively small. For instance, the ratio of bore diameter to outside diameter can range upwardly to about 0.3, preferably, from about 0.01 to about 0.25 and, most preferably, from about 0.02 to about 0.2.

Typically, the outside diameter of the hollow cylinder is in the range of from 4 to 16 mm, more typically from 5 to 12 mm, for example about 8 mm. In another embodiment, the outside diameter of the hollow cylinder is typically in the range of from 4 to 12 mm, more typically from 5 to 10 mm, for example about 8 mm. Typically, the bore diameter is smaller than 3.5 mm, more typically in the range of from 0.01 to 3 mm, for example in the range of from about 0.1 mm to about 2.5 mm, more typically from about 0.2 mm to about 2 mm, for example about 1 mm or about 1.5 mm.

In addition to the support material that is formed into an agglomerate having a specific geometric configuration, incorporated into the support material is at least a catalytically effective amount of silver and, optionally, one or more promoters and, optionally, one or more copromoters. Thus, the inventive catalyst comprises a shaped support material, a catalytically effective amount of silver and, optionally, one or more promoters and, optionally, one or more copromoters.

Another particular aspect of the inventive catalyst is for the support to be typically highly loaded with silver. The combination of using a high porosity support material having the shaped configuration, in combination, helps provide for a high silver loading. The silver loading is generally such that the amount of silver in the catalyst composition exceeds about 15 weight percent based on the total weight of the catalyst or even exceeding 16 weight percent. Preferably, however, the silver content of the catalysts exceeds 17 weight percent and, more preferably 18 weight percent, and most preferably 20 weight percent. Typically, the amount of silver is at most 50 weight percent, more typically at most 45 weight percent, in particular at most 40 weight percent, based on the total weight of the catalyst.

In general, the catalyst of the present invention is prepared by impregnating the shaped agglomerate of support material with silver and, optionally, one or more promoters, such as, for example, rare earth metals, magnesium, rhenium and alkali metals (lithium, sodium, potassium, rubidium and cesium), or compounds thereof, and, optionally, one or more copromoters, such as, for example, sulfur, molybdenum, tungsten and chromium, or compounds thereof. Among the promoter components that can be incorporated into the shaped agglomerate of support material, rhenium and the alkali metals, in particular, the higher alkali metals, such as potassium, rubidium and cesium, are preferred. Most preferred among the higher alkali metals is cesium, which may be used alone or in a mixture together with for example potassium and/or lithium. Either the rhenium promoter may be used without an alkali metal promoter being present or an alkali metal promoter may be used without a rhenium promoter being present or a rhenium promoter and an alkali metal promoter can both be present in the catalyst system. The copromoters for use in combination with rhenium can include sulfur, molybdenum, tungsten, and chromium.

Silver is incorporated into the shaped agglomerate of support material by contacting it with a silver solution formed by dissolving a silver salt, or silver compound, or silver complex in a suitable solvent. The contacting or impregnation is preferably done in a single impregnation step whereby the silver is deposited onto the shaped agglomerate so as to provide, for instance, at least about 15 weight percent silver, based on the total weight of the catalyst. In another preferred embodiment, wherein a substantially higher amount of silver is deposited onto the shaped agglomerate, for instance, at least 20 weight percent silver, based on the total weight of the catalyst, silver may be deposited in more than one impregnation step, for example in two, three or four impregnation steps, preferably two impregnation steps.

The one or more promoters can also be deposited on the shaped agglomerate either prior to, coincidentally with, or subsequent to the deposition of the silver, but, preferably, the one or more promoters are deposited on the shaped agglomerate coincidentally or simultaneously with the silver. When the catalyst comprises silver, rhenium and a copromoter for rhenium, it may be advantageous to deposit the copromoter prior to or simultaneous with the deposition of silver, and to deposit rhenium after at least a portion of the silver has been deposited. The advantage is this sequence of deposition steps materializes in an enhanced stability of the catalyst in particular in respect of its activity.

Promoting amounts of alkali metal or mixtures of alkali metal can be deposited on a shaped agglomerate support using a suitable solution. Although alkali metals exist in a pure metallic state, they are not suitable for use in that form. They are generally used as compounds of the alkali metals dissolved in a suitable solvent for impregnation purposes. The shaped agglomerate may be impregnated with a solution of the alkali metal compound(s) before, during or after impregnation of the silver in a suitable form has taken place. An alkali metal promoter may even be deposited on the shaped agglomerate after the silver component has been reduced to metallic silver.

The promoting amount of alkali metal utilized will depend on several variables, such as, for example, the surface area and pore structure and surface chemical properties of the carrier used, the silver content of the catalyst and the particular ions and their amounts used in conjunction with the alkali metal cation.

The amount of alkali metal promoter deposited upon the shaped agglomerate or present on the catalyst is generally in the range of from about 10 parts per million to about 3000 parts per million, preferably between about 15 parts per million and about 2000 parts per million and more preferably, between about 20 parts per million and about 1500 parts per million, by weight of the metal relative to the weight of total catalyst.

The shaped agglomerate can also be impregnated with rhenium ions, salt(s), compound(s), and/or complex(es). This may be done at the same time that the alkali metal promoter is added, or before or later; or at the same time that the silver is added, or before or later. Rhenium, alkali metal, and silver may be in the same impregnation solution. Their presence in different solutions will provide suitable catalysts, and in some instances even improved catalysts.

The preferred amount of rhenium, calculated as the metal, deposited on or present on the shaped agglomerate or catalyst ranges from about 0.1 micromoles (μmole) per gram to about 10 micromoles per gram, more preferably from about 0.2 micromoles per gram to about 5 micromoles per gram of total catalyst, or, alternatively stated, from about 19 parts per million to about 1860 parts per million, preferably from about 37 parts per million to about 930 parts per million by weight of total catalyst. The references to the amount of rhenium present on the catalyst are expressed as the metal, irrespective of the form in which the rhenium is actually present.

The rhenium compound used in the preparation of the instant catalyst includes rhenium compounds that can be solubilized in an appropriate solvent. Preferably, the solvent is a water-containing solvent. More preferably, the solvent is the same solvent used to deposit the silver and the alkali metal promoter.

Examples of suitable rhenium compounds used in making the inventive catalyst include the rhenium salts such as rhenium halides, the rhenium oxyhalides, the rhenates, the perrhenates, the oxides and the acids of rhenium. A preferred compound for use in the impregnation solution is the perrhenate, preferably ammonium perrhenate. However, the alkali metal perrhenates, alkaline earth metal perrhenates, silver perrhenates, other perrhenates and rhenium heptoxide can also be suitably utilized.

The one or more copromoters can be deposited on the shaped agglomerate by any suitable manner known to those skilled in the art. The copromoter is deposited on the shaped agglomerate either prior to, coincidentally with, or subsequent to the deposition of the silver, but preferably, the one or more copromoters are deposited on the shaped agglomerate coincidentally or simultaneously with the silver. A copromoting amount of copromoter is deposited on the shaped agglomerate and can generally be in the range of from about 0.01 to about 25, or more, μmoles per gram of total catalyst.

The catalysts according to the present invention have a particularly high activity and high selectivity for ethylene oxide production in the direct oxidation of ethylene with molecular oxygen to ethylene oxide. For instance, the inventive catalyst can have an initial selectivity of at least about 86.5 mole percent, preferably, at least 87 mole percent and, most preferably, at least 88.5 mole percent. It is a benefit of this invention that when packing the inventive catalyst into a catalyst bed it provides a catalyst bed having a relatively high silver loading, without causing an increased pressure drop over the catalyst bed when in use in the process for manufacturing ethylene oxide, and/or having an improved balance of packing density relative to such pressure drop. When decreasing the bore diameter, the balance of pressure drop/packing density behaves favorably in a typical reactor tube used in the manufacture of ethylene oxide, compared with predictions on the basis of theoretical models, for example the Ergun Correlation, see W. J. Beek and K. M. K. Muttzall, "Transport Phenomena", J. Wiley and Sons Ltd, 1975, p. 114. By practicing the present invention, it is achievable that the silver loading of the catalyst may be at least 150 kg silver/$m^3$ catalyst bed, preferably at least 170 kg silver/$m^3$ catalyst bed, more preferably at least 200 kg silver/$m^3$ catalyst bed, and in particular at least 250 kg silver/$m^3$ catalyst bed. Frequently, the silver loading is at most 800 kg silver/$m^3$ catalyst bed, more frequently at most 600 kg silver/$m^3$ catalyst bed, still more frequently at most 550 kg silver/$m^3$ catalyst bed. The high silver loading permits the application of relatively mild conditions in the process for manufacturing ethylene oxide, in particular temperature, for the achievement of a given work rate, along with the achievement of an improved selectivity and catalyst life, in particular in terms of activity stability and selectivity stability.

As it is used herein with reference to the selectivity of a catalyst, the term "selectivity", $S_w$, means the mole percent (%) of the desired ethylene oxide formed relative to the total of ethylene converted. The selectivity may be specified at a given work rate, w, for a catalyst with the work rate being defined as the amount of ethylene oxide produced per unit volume of catalyst (e.g., kg per $m^3$) per hour. As it is used herein with reference to the activity of a catalyst, the term "activity", $T_w$, means the temperature needed to reach a given work rate.

The conditions for carrying out the epoxidation reaction in the presence of the catalysts according to the present invention broadly comprise those already described in the prior art. This applies, for example, to suitable temperatures, pressures, residence times, diluent materials such as nitrogen, carbon dioxide, steam, argon, methane or other saturated hydrocarbons, to the presence of moderating agents to control the catalytic action, for example, 1,2-dichloroethane, vinyl chloride, ethyl chloride or chlorinated polyphenyl compounds, to the desirability of employing recycle operations or applying successive conversions in different reactors to increase the yields of ethylene oxide, and to any other special conditions which may be selected in processes for preparing ethylene oxide. Pressures in the range of from atmospheric to about 3450 kPa gauge (500 psig) are generally employed. Higher pressures, however, are not excluded. The molecular oxygen employed as reactant can be obtained from any suitable source including conventional sources. A suitable oxygen charge can include relatively pure oxygen, or a concentrated oxygen stream comprising oxygen in major amount with lesser amounts of one or more diluents, such as nitrogen and argon, or any other oxygen-containing stream, such as air. The use of the present catalysts in ethylene oxide reactions is in no way limited to the use of specific conditions among those that are known to be effective.

For purposes of illustration only, the following table shows the range of conditions that are often used in current commercial ethylene oxide reactor units.

TABLE I

| | |
|---|---|
| *GHSV | 1500-10,000 |
| Inlet Pressure | 1034-2758 kPa gauge (150-400 psig) |
| Inlet Feed | |
| Ethylene | 1-50%, or 1-40% |
| Oxygen | 3-12% |
| Carbon dioxide | 0-15% |
| Ethane | 0-3% |
| Argon and/or methane and/or nitrogen | Balance |
| Diluent chlorohydrocarbon moderator | 0.3-20 ppmv total |
| Coolant temperature | 180-315° C. |
| Catalyst temperature | 180-325° C. |
| $O_2$ conversion level | 10-60% |
| Ethylene Oxide (EO) Production (Work Rate) | 32-320 kg EO/($m^3$ catalyst.hour) (2-20 lbs. EO/cu. ft. catalyst/hr.) |

*Cubic meters of gas at standard temperature and pressure passing over one cubic meter of packed catalyst per hour (cubic feet of gas at standard temperature and pressure passing over one cubic foot of packed catalyst per hour).

In a preferred application, ethylene oxide is produced when an oxygen-containing gas is contacted with ethylene in the presence of the inventive catalysts under suitable epoxidation reaction conditions such as at a temperature in the range of from about 180° C. to about 330° C., and, preferably, 200° C. to 325° C., and a pressure in the range of from atmospheric to about 3450 kPa gauge (500 psig) and, preferably, from 1034 kPa to 2758 kPa gauge (150 psig to 400 psig). In the normal practice of the process for manufacturing ethylene oxide, the feed stream which is contacted with the catalyst, and which comprises ethylene and oxygen, comprises in addition a low concentration of carbon dioxide, because carbon dioxide is a byproduct of the process and appears, in part, in the feed stream as a result of recycling. It is advantageous to reduce in the feed stream the concentration of carbon dioxide to a low level, as this will further enhance the catalyst performance in terms of activity, selectivity and catalyst life. It is preferred that the quantity of carbon dioxide in the feed is at most 4 mole-%, more preferred at most 2 mole-%, in particular at most 1 mole-%, relative to the total feed. Frequently the quantity of carbon dioxide will be at least 0.1 mole-%, more frequently at least 0.5 mole-%, relative to the total feed.

The ethylene oxide produced may be recovered from the reaction mixture by using methods known in the art, for example by absorbing the ethylene oxide from the reactor outlet stream in water and optionally recovering the ethylene oxide from the aqueous solution by distillation.

The ethylene oxide produced in the epoxidation process may be converted into ethylene glycol, an ethylene glycol ether or an alkanolamine.

The conversion into the ethylene glycol or the ethylene glycol ether may comprise, for example, reacting the ethylene oxide with water, suitably using an acidic or a basic catalyst. For example, for making predominantly the ethylene glycol and less ethylene glycol ether, the ethylene oxide may be reacted with a ten fold molar excess of water, in a liquid phase reaction in presence of an acid catalyst, e.g. 0.5-1.0% w sulfuric acid, based on the total reaction mixture, at 50-70° C. at 100 kPa absolute, or in a gas phase reaction at 130-240° C. and 2000-4000 kPa absolute, preferably in the absence of a catalyst. If the proportion of water is lowered the proportion of ethylene glycol ethers in the reaction mixture is increased. The ethylene glycol ethers thus produced may be a di-ether, tri-ether, tetra-ether or a subsequent ether. Alternative ethylene glycol ethers may be prepared by converting the ethylene oxide with an alcohol, in particular a primary alcohol, such as methanol or ethanol, by replacing at least a portion of the water by the alcohol.

The conversion into the alkanolamine may comprise reacting ethylene oxide with an amine, such as ammonia, an alkyl amine or a dialkylamine. Anhydrous or aqueous ammonia may be used. Anhydrous ammonia is typically used to favor the production of monoalkanolamine. For methods applicable in the conversion of ethylene oxide into the alkanolamine, reference may be made to, for example U.S. Pat. No. 4,845,296, which is incorporated herein by reference.

Ethylene glycol and ethylene glycol ethers may be used in a large variety of industrial applications, for example in the fields of food, beverages, tobacco, cosmetics, thermoplastic polymers, curable resin systems, detergents, heat transfer systems, etc. Alkanolamines may be used, for example, in the treating ("sweetening") of natural gas.

The following examples are intended to illustrate the advantages of the present invention and are not intended to unduly limit the scope of the invention.

EXAMPLE I

This Example I describes the preparation of a stock silver impregnation solution used for impregnating various support materials as described in the following examples.

In a 5-liter stainless steel beaker 415 grams of reagent grade sodium hydroxide was dissolved in 2340 ml of deionized water. The temperature of the solution was adjusted to about 50° C. In a 4-liter stainless steel beaker 1699 grams of silver nitrate was dissolved in 2100 ml of deionized water. The temperature of the solution was adjusted to about 50° C. The sodium hydroxide solution was slowly added to the silver nitrate solution with stirring while the temperature was maintained at about 50° C. The resulting slurry was stirred for about 15 minutes. The pH of the solution was maintained at above 10 by the addition of NaOH solution as required. A washing procedure was used which included removing liquid by the use of a filter wand followed by the replacement of the removed liquid with an equivalent volume of deionized water. This washing procedure was repeated until the conductivity of the filtrate dropped below 90 micro-mho/cm. After the completion of the last wash cycle, 1500 ml of deionized water was added and followed by the addition of 630 grams of oxalic acid dihydrate (4.997 moles) in increments of 100 grams while stirring and maintaining the solution at about 40° C. (±5° C.). The pH of the solution was monitored during the addition of the last 130 grams of oxalic acid dihydrate to ensure that it did not drop below 7.8 for an extended period of time. Water was removed from the solution with a filter wand and the slurry was cooled to less than 30° C. Slowly added to the solution was 732 grams of 92% ethylenediamine (EDA). The temperature was maintained below 30° C. during this addition. A spatula was used to manually stir the mixture until enough liquid was present to mechanically stir. The final solution was used as a stock silver impregnation solution for preparing the catalysts of Example III.

EXAMPLE II

This Example II presents information concerning the properties and geometric configuration of the four carriers (i.e., Carrier A, Carrier B, Carrier C, and Carrier D) used in the preparation of the catalysts as described in Example III. Presented in the following Table II are certain properties of each of the carriers.

TABLE II

| Properties of Carriers | | | | |
|---|---|---|---|---|
| | Carrier A | Carrier B | Carrier C | Carrier D |
| Properties | | | | |
| Water Absorption, % | 39.2 | 45.6 | 46.5 | 50.4 |
| Bulk Packing Density, kg/m$^3$ (lbs/ft$^3$) | 805 (50.3) | 728 (45.5) | 843 (52.7) | 788 (49.2) |
| ASTM Attrition Loss, % | 10.8 | 14.6 | 14.7 | 16.5 |
| Average Flat Plate Crush Strength, N (lbf) | 127 (28.6) | 95 (21.4) | 130 (29.3) | 180 (40.4) |
| Surface Area, m$^2$/g | 0.80 | 0.78 | 0.77 | 0.78 |
| Geometric Configuration | | | | |
| Nominal Size, mm | 8 | 8 | 8 | 8 |
| Average Length, mm | 8.1 | 8.1 | 7.7 | 7.7 |
| Length, Range, mm | | 7.6-8.8 | 6.6-8.6 | 6.6-8.6 |
| Diameter, mm | 8.5 | 8.5 | 8.6 | 8.6 |
| Bore Diameter, mm | 3.8 | 3.8 | 1.02 | 1.02 |
| Ratio Length/Outside Diameter | approx. 1 | 0.95 | 0.90 | 0.90 |

Each carrier presented in the above Table II had a nominal size of 8 mm and a hollow cylinder geometric configuration. The bore diameter of both Carrier A and Carrier B was 3.8 mm, while the bore diameter of Carriers C and D was only 1 mm. The water pore volumes of Carriers B, C, and D were significantly greater than the water pore volume of Carrier A. This explains the reduction in crush strength and packing density of Carrier B relative to Carrier A; however, with the reduction of the bore diameter of Carriers C and D relative to both Carrier A and Carrier B, the crush strength and packing density are improved such that these properties have values that exceed such values for Carrier A. Carrier D is an example of further improvement over Carrier C, with increased pore volume for the small bore diameter type carrier. This allows for significantly higher silver loadings on the finished catalyst, especially when multiple impregnation techniques are employed in the catalyst preparation.

EXAMPLE III

This Example III describes the preparation of the comparison catalyst and the inventive catalysts and certain of their physical properties.

Catalyst A (For Comparison):

The impregnation solution for preparing Catalyst A was made by mixing 153 grams of silver stock solution of specific gravity 1.5673 g/ml with a solution of 0.1235 g of $NH_4ReO_4$ in 2 g of 1:1 $EDA/H_2O$, 0.0574 g of ammonium metatungstate dissolved in 2 g of 1:1 ammonia/water and 0.3174 g $LiNO_3$ dissolved in water. Additional water was added to adjust the specific gravity of the solution to 1.465 g/ml. 50 grams of such doped solution was mixed with 0.1016 g of 50% CsOH solution. This final impregnation solution was used to prepare Catalyst A. 30 grams of Carrier A was evacuated to 20 mm Hg for 1 minute and the final impregnation solution was added to Carrier A while under vacuum, then the vacuum was released and the carrier allowed to contact the liquid for 3 minutes. The impregnated Carrier A was then centrifuged at 500 rpm for 2 minutes to remove excess liquid. Subsequently, impregnated Carrier A was placed in a vibrating shaker and dried in flowing air at 250° C. for 5½ minutes. The final Catalyst A composition was 13.2% Ag, 460 ppm Cs/g catalyst, 1.5 µmole Re/g catalyst, 0.75 µmole W/g catalyst, and 15 µmole Li/g catalyst.

Catalyst B (For Comparison):

The impregnation solution for preparing Catalyst B was made by mixing 153 grams of silver stock solution of specific gravity 1.589 g/ml with a solution of 0.1051 g of $NH_4ReO_4$ in 2 g of 1:1 $EDA/H_2O$, 0.0488 g of ammonium metatungstate dissolved in 2 g of 1:1 ammonia/water and 0.270 g $LiNO_3$ dissolved in water. Additional water was added to adjust the specific gravity of the solution to 1.588 g/ml. 50 grams of such doped solution was mixed with 0.0940 g of 50% CsOH solution. This final impregnation solution was used to prepare Catalyst B. 30 grams of Carrier B was evacuated to 20 mm Hg for 1 minute and the final impregnation solution was added to Carrier B while under vacuum, then the vacuum was released and the carrier allowed to contact the liquid for 3 minutes. The impregnated Carrier B was then centrifuged at 500 rpm for 2 minutes to remove excess liquid. Subsequently, impregnated Carrier B was placed in a vibrating shaker and dried in flowing air at 250° C. for 5½ minutes. The final Catalyst B composition was 17.5% Ag, 500 ppm Cs/g catalyst, 1.5 µmole Re/g catalyst, 0.75 µmole W/g catalyst, and 15 µmole Li/g catalyst.

Catalyst C (According to the Invention):

The impregnation solution for preparing Catalyst C was made by mixing 204 grams of silver stock solution of specific gravity 1.573 g/ml with a solution of 0.1378 g of $NH_4ReO_4$ in 2 g of 1:1 $EDA/H_2O$, 0.064 g of ammonium metatungstate dissolved in 2 g of 1:1 ammonia/water and 0.3542 g $LiNO_3$ dissolved in water. Additional water was added to adjust the specific gravity of the solution to 1.558 g/ml. 50 grams of such doped solution was mixed with 0.0850 g of 50% CsOH solution. This final impregnation solution was used to prepare Catalyst C. 30 grams of Carrier C was evacuated to 20 mm Hg for 1 minute and the final impregnation solution was added to Carrier C while under vacuum, then the vacuum was released and the carrier allowed to contact the liquid for 3 minutes. The impregnated Carrier C was then centrifuged at 500 rpm for 2 minutes to remove excess liquid. Subsequently, impregnated Carrier C was placed in a vibrating shaker and dried in flowing air at 250° C. for 7 minutes. The final Catalyst C composition was 17.8% Ag, 460 ppm Cs/g catalyst, 1.5 µmole Re/g catalyst, 0.75 µmole W/g catalyst, and 15 µmole Li/g catalyst.

Catalyst D (According to the Invention):

Catalyst D was prepared in two impregnation steps: the first step involving impregnation with silver, without dopants, the second step involving impregnation with silver and the dopants. Approximately 120 grams of Carrier C was first impregnated with 204 grams of silver solution having a specific gravity of 1.53 g/ml according to the procedure for catalyst C, except that no dopants were added to the silver solution. The resulting dried catalyst precursor contained approximately 17 wt % silver. The dried Catalyst D Precursor was then impregnated with a second solution which was made by mixing 191.0 grams of silver stock solution of specific gravity 1.53 g/ml with a solution of 0.2915 g of $NH_4ReO_4$ in 2 g of 1:1 $EDA/H_2O$, 0.0678 g of ammonium metatungstate dissolved in 2 g of 1:1 ammonia/water and 0.3747 g $LiNO_3$ dissolved in water. Additional water was added to adjust the specific gravity of the solution to 1.48 g/ml. 50 grams of such doped solution was mixed with 0.1397 g of 45.4 wt % CsOH solution. This final impregnation solution was used to prepare Catalyst D. A flask containing 30 grams of the Catalyst D Precursor was evacuated to 20 mm Hg for 1 minute and the final impregnation solution was added while under vacuum, then the vacuum was released and the precursor allowed to contact the liquid for 3 minutes. The impregnated precursor was then centrifuged at 500 rpm for 2 minutes to remove excess liquid. Subsequently, Catalyst D was placed in a vibrating shaker and dried in air flowing at a rate of 217 Nl/min (460 SCFH) at 250° C. for 7 minutes. The final Catalyst D composition was 27.3% Ag, 550 ppm Cs/g catalyst, 2.4 µmole Re/g catalyst, 0.60 µmole W/g catalyst, and 12 µmole Li/g catalyst.

Catalyst E (According to the Invention):

Catalyst E was prepared in two impregnation steps: the first step involving impregnation with silver and a tungsten dopant, the second step involving impregnation with silver and the other dopants. Ammonium metatungstate (0.0639 g) was first dissolved in 1 gram of 33 wt % ethylenediammine/water mixture. This solution was added to 200 grams of a silver solution prepared according to the procedure in Example 1, and having a specific gravity of 1.523 g/ml. Carrier C was impregnated with this silver solution, then centrifuged and dried according to the procedure for catalyst C. The resulting dried Catalyst E Precursor contained approximately 16.6 wt % silver. This dried Catalyst E Precursor was then impregnated with a second solution which was made by mixing 200 grams of silver stock solution of specific gravity 1.523 g/ml with a solution of 0.2906 g of $NH_4ReO_4$ in 1 g of 1:1 $EDA/H_2O$, and 0.3735 g $LiNO_3$ dissolved in 1 gram water. Additional water was added to adjust the specific gravity of the solution to 1.49 g/ml. 50 grams of such doped solution was mixed with 0.1416 g of 44.6 wt % CsOH solution. This final impregnation solution was used to prepare Catalyst E. A flask containing 30 grams of the Catalyst E Precursor was evacuated to 20 mm Hg for 1 minute and the final impregnation solution was added to the Catalyst E Precursor while under vacuum, then the vacuum was released and the Precursor allowed to contact the liquid for 3 minutes. The impregnated Catalyst E Precursor was then centrifuged at 500 rpm for 2 minutes to remove excess liquid, and subsequently placed in a vibrating shaker and dried in air flowing at a rate of 460 SCFH at 250° C. for 7 minutes. The final Catalyst E composition was 27.3% Ag, 560 ppm Cs/g catalyst, 2.4 μmole Re/g catalyst, 0.60 μmole W/g catalyst, and 12 μmole Li/g catalyst.

Presented in Table III are the silver loadings of each of the catalysts. It is noted that the silver component of the inventive catalysts B and C was incorporated into the support material by single impregnation methods. Catalyst B includes a significantly higher amount of silver than does Catalyst A. This is thought to be due to the higher water absorption of Carrier B as compared to Carrier A. As for Catalyst C, while it contains close to the same weight percent silver as does Catalyst B, a greater total amount of silver is able to be loaded into a given reactor volume with Catalyst C as opposed to Catalyst A or Catalyst B due to the modified geometry. Catalysts D and E illustrate the loadings achievable with multiple impregnation methods on Carrier C. These examples represent double impregnation results, and it is understood that more impregnations would result in yet higher silver levels. It is also understood that employing a carrier such as Carrier D would result in yet higher silver levels.

TABLE III

Silver Content of Catalyst Systems

|  | Weight % Silver in Catalyst | Silver Loading in 39 mm Packed Bed, kg/m³ |
|---|---|---|
| Catalyst A *) | 13.2 | 116 |
| Catalyst B *) | 17.5 | 146 |
| Catalyst C **) | 17.8 | 173 |
| Catalyst D **) | 27.3 | 300 |
| Catalyst E **) | 27.3 | 300 |

*) for comparison
**) according to the invention

Table III also presents the silver loadings of packed catalyst beds which can be achieved when packing the Catalysts A, B, C, D and E in a 39-mm tubular reactor, which is a typical size for use in conjunction with catalysts on a support material of this size. It can be seen that, advantageously, the silver loading in the packed catalyst bed (and in a commercial reactor the amounts of silver packed per unit reactor volume) will be higher as the silver content of the catalyst and the packing density of the catalyst is higher.

EXAMPLE IV

This Example IV describes the procedure for testing certain of the catalytic properties, such as, selectivity and activity, of the catalysts described in Example III.

Catalysts A, B, C, D, and E were tested for their ability to produce ethylene oxide from a feed containing ethylene and oxygen. To do this, 4 to 5.3 g of crushed catalyst was loaded into a 6.4 mm (¼ inch) stainless steel U-shaped reactor tube. The tube was immersed in a molten metal bath (heat medium) and the ends were connected to a gas flow system. The weight of catalyst used and the inlet gas flow rate were adjusted to give a gas hourly space velocity of 3300 Nl/(l.h), as calculated for uncrushed catalyst. As for the uncrushed catalysts the catalyst packing density and silver loading changes, the amount of crushed catalyst loaded in the test reactor was changed to reflect different amounts of silver packed per unit reactor volume when using the uncrushed catalysts in a commercial reactor. The catalyst loadings were as follows: Catalyst A (comparative) 4.2 grams, Catalyst B (comparative) 4.01 g, Catalyst C (invention) 4.66 g, Catalyst D (invention) 5.29 g, and Catalyst E (invention) 5.29 g. The gas flow was 16.9 Nl/h. The inlet gas pressure was 1550 kPa. The catalysts were treated with nitrogen at 225° C. for 2 hours prior to testing. The testing gas mixture passed through the catalyst bed, in a "once-through" operation, consisted of 30% v ethylene, 8% v oxygen, 5% v carbon dioxide, 57% v nitrogen and 1.5 to 6.0 parts by million by volume (ppmv) ethyl chloride. The temperature was adjusted such that the ethylene oxide concentration in the reactor outlet was 3.1 mole-%. Ethyl chloride concentration was adjusted to obtain maximum selectivity.

The initial performance, i.e. selectivity and activity, of the catalysts is reported in Table IV. The initial performance reflects the performance level of the catalyst as it lined out during the initial two-weeks of testing. The activity as specified reflects the temperature at which the concentration of ethylene oxide in the reactor outlet is 3.1 mole-%. A lower temperature is indicative of a higher activity.

In the testing of Catalysts A, C, D and E the activity and selectivity were also measured upon continued operation. The results obtained after a cumulative production of ethylene oxide of 0.6 kton/m³ and 1.4 kton/m³ of catalyst are also reported in Table IV.

TABLE IV

Catalytic Performance of Catalysts

|  | Selectivity Percent (%) | Activity Temp (° C.) |
|---|---|---|
| Catalyst A *), initially | 88.0 | 262 |
| at 0.6 kton/m³ | 88.5 | 275 |
| at 1.4 kton/m³ | 73.0 | 300 |
| Catalyst B *), initially | 89.1 | 263 |
| Catalyst C **) | 89.4 | 254 |
| at 0.6 kton/m³ | 87.0 | 270 |
| at 1.4 kton/m³ | 79.5 | 285 |
| Catalyst D **), initially | 89.0 | 246 |
| at 0.6 kton/m³ | 88.0 | 264 |
| at 1.4 kton/m³ | 81.0 | 278 |
| Catalyst E **), initially | 87.5 | 248 |
| at 0.6 kton/m³ | 87.0 | 254 |
| at 1.4 kton/m³ | 79.5 | 268 |

*) for comparison
**) according to the invention

As can be seen from the catalyst performance data presented in Table IV, Catalyst C demonstrates a substantial improvement in initial selectivity relative to Catalyst A and Catalyst B. Catalyst C also demonstrates a substantially greater initial activity than both Catalyst A and Catalyst B by requiring a significantly lower reaction temperature that gives a significantly greater selectivity. It is believed that the improved initial performance of Catalyst C over that of both Catalyst A and Catalyst B is attributable to the greater amount of silver that can be packed into a reactor due to the high silver loading achievable with the catalyst having a higher water absorption. The improved activity is believed to result from the use of a support material having a hollow cylinder geometric configuration with a small bore diameter in the manufacture of the catalyst.

It is further shown that the concept of higher silver in the specific support geometries can be extended to multiple impregnation methods of catalyst preparation. Catalyst D clearly illustrates the initial selectivity and activity advantage over Catalyst A, and an activity advantage over Catalysts A, B, and C. Also, Catalyst E has a markedly improved initial activity over Catalysts A, B, and C. Both multiple impregnation examples show particularly well the performance improvement as a result of the additional silver loading in an equal reactor volume. Catalyst E illustrates how the advantage in activity can be maintained with respectable selectivity when the dopant addition is sequenced between two impregnation steps.

The performance data obtained for the Catalysts A, C, D and E upon continued operation indicate that Catalyst E provides a further advantage with respect to stability over Catalyst D. The improvement in activity stability is evident from the data in Table IV.

While this invention has been described in terms of the presently preferred embodiment, reasonable variations and modifications are possible by those skilled in the art. Such variations and modifications are within the scope of the described invention and the appended claims.

That which is claimed is:

1. A catalyst, which catalyst comprises silver deposited on a shaped support material having a hollow cylinder geometric configuration such that the length-to-outside diameter ratio of said shaped support material is in the range of from about 0.3 to about 2 and the internal diameter is in the range upwardly to 30 percent of the outside diameter of said shaped support material.

2. A catalyst as recited in claim 1, wherein silver is present in a quantity in the range exceeding 15 weight percent of the total weight of the catalyst.

3. A catalyst as recited in claim 2, wherein silver is present in a quantity in the range of exceeding 20 weight percent to and at most 50 weight percent, of the total weight of the catalyst.

4. A catalyst as recited in claim 1, wherein the support material has a water absorption exceeding 40%.

5. A catalyst as recited in claim 1, wherein the support material has a surface area in the range of from 0.03 $m^2/g$ to 10 $m^2/g$.

6. A catalyst as recited in claim 1, wherein the support material has a water absorption in the range of from 42.5% to 80%, and a surface area in the range of from 0.5 $m^2/g$ to 5 $m^2/g$.

7. A catalyst as recited in claim 1, wherein the length-to-outside diameter ratio is in the range of from about 0.5 to about 1.6 and the ratio of internal diameter to outside diameter is in the range of from 0.01 to 0.25.

8. A catalyst as recited in claim 7, wherein the length-to-outside diameter ratio is in the range of from about 0.9 to about 1.1 and the ratio of internal diameter to outside diameter is in the range of from 0.02 to 0.2.

9. A catalyst as recited in claim 1, wherein the outside diameter is in the range of from 4 to 16 mm, and the bore diameter is smaller than 3.5 mm.

10. A catalyst as recited in claim 1, wherein the outside diameter is in the range of from 5 to 12 mm, and the bore diameter is in the range of from 0.1 to 3 mm.

11. A catalyst as recited in claim 1, wherein the bore diameter is in the range of from about 0.2 mm to about 2 mm.

12. A catalyst as recited in claim 1, wherein the catalyst further comprises a promoter component comprising a rare earth metal, magnesium, rhenium, or an alkali metal.

13. A catalyst as recited in claim 1, wherein the catalyst further comprises a promoter component comprising rhenium, an alkali metal selected from lithium, potassium, rubidium and cesium, and, in addition, a rhenium copromoter comprising sulfur, molybdenum, tungsten or chromium.

14. A method, comprising:
    providing a shaped support material having a geometric configuration such that the length-to-outside diameter ratio is in the range of from about 0.3 to about 2 and the internal diameter is in the range upwardly to 30 percent of the outside diameter of said shaped catalyst support; and
    depositing silver on the shaped support.

15. A method as recited in claim 14, comprising depositing on the support, in addition to silver, a promoter component comprising rhenium, and a rhenium copromoter comprising sulfur, molybdenum, tungsten or chromium, wherein the rhenium copromoter is deposit prior to or simultaneous with the deposition of silver, and rhenium is deposited after at least a portion of the silver has been deposited.

* * * * *